(12) United States Patent
Hsu

(10) Patent No.: US 11,344,332 B2
(45) Date of Patent: May 31, 2022

(54) PORTABLE MULTI-FUNCTIONAL NON-INVASIVE BLACKHEAD REMOVER APPARATUS

(71) Applicant: Raymond Hsu, Shenzhen (CN)

(72) Inventor: Raymond Hsu, Shenzhen (CN)

( * ) Notice: Subject to any disclaimer, the term of this patent is extended or adjusted under 35 U.S.C. 154(b) by 308 days.

(21) Appl. No.: 16/295,839

(22) Filed: Mar. 7, 2019

(65) Prior Publication Data

US 2020/0187986 A1 Jun. 18, 2020

Related U.S. Application Data

(63) Continuation-in-part of application No. 29/673,389, filed on Dec. 14, 2018, now abandoned.

(51) Int. Cl.
*A61B 17/50* (2006.01)
*A61H 7/00* (2006.01)
(Continued)

(52) U.S. Cl.
CPC ............. *A61B 17/50* (2013.01); *A61H 7/003* (2013.01); *A61H 7/008* (2013.01); *A46B 13/008* (2013.01);
(Continued)

(58) Field of Classification Search
CPC .................... A61H 7/003; A61H 23/02; A61H 2201/0107; A61H 2201/1685;
(Continued)

(56) References Cited

U.S. PATENT DOCUMENTS

2006/0253078 A1* 11/2006 Wu .................... A61M 37/0015
604/173
2014/0142472 A1* 5/2014 Giraud ................... A61H 7/007
601/18
(Continued)

FOREIGN PATENT DOCUMENTS

CN 209033281 U * 6/2019
WO WO-2017114929 A1 * 7/2017 ............. A61H 15/02

OTHER PUBLICATIONS

"Housing." Merriam-Webster.com Dictionary, Merriam-Webster, https://www.merriam-webster.com/dictionary/housing. Accessed Feb. 17, 2021. (Year: 2021).*
(Continued)

*Primary Examiner* — Andrew J Mensh
*Assistant Examiner* — Nhu Q. Tran
(74) *Attorney, Agent, or Firm* — Alexander Chen, Esq.

(57) ABSTRACT

An apparatus for removing blackheads and providing skin care treatments comprising a funnel body that comprises a compartment, a first opening and a second opening that are bended about 45 degrees from an axial axis. The first opening further comprises a vacuum tip that is detachable and the second opening further comprises a massage metal plate. The apparatus further comprises a vacuum pump, a CPU, and a PCB. The vacuum tip further comprises a vacuum filter. The funnel body further comprises a smart switch disposed on the outside wall thereof. The apparatus further comprises a lithium battery. The funnel body further comprises vent pores. The apparatus further comprises a status light made of LED.

2 Claims, 7 Drawing Sheets

(51) Int. Cl.
*A46B 13/00* (2006.01)
*A61H 23/02* (2006.01)

(52) U.S. Cl.
CPC ........ *A46B 2200/102* (2013.01); *A61H 23/02* (2013.01); *A61H 2201/0107* (2013.01); *A61H 2201/1685* (2013.01); *A61H 2205/022* (2013.01)

(58) Field of Classification Search
CPC .............. A61H 7/008; A61H 2205/022; A61H 2201/5097; A61H 2201/0153; A61H 2201/1207; A61H 2201/0157; A46B 13/008; A46B 2200/102; A61M 1/0003; A61M 1/0005; A61M 1/0039; A61M 2210/0618; A61M 2210/04; A61M 2210/0662; A61M 2210/0668; A61B 17/50; A61B 2017/00761
USPC ........................................................ 604/313
See application file for complete search history.

(56) References Cited

U.S. PATENT DOCUMENTS

| | | | |
|---|---|---|---|
| 2016/0302963 A1* | 10/2016 | Yang ...................... | A61H 23/00 |
| 2016/0331308 A1* | 11/2016 | Zhou ..................... | A61B 5/0022 |
| 2018/0099143 A1* | 4/2018 | Kim ...................... | A61N 5/0616 |
| 2018/0126160 A1* | 5/2018 | Hyun ................... | A61N 1/0476 |
| 2018/0228688 A1* | 8/2018 | Kang ................... | B01D 46/001 |
| 2020/0038530 A1* | 2/2020 | Yildirim ............... | A61L 2/0094 |
| 2020/0179220 A1* | 6/2020 | Jablow ................... | A61H 1/00 |
| 2020/0222269 A1* | 7/2020 | Rodan ................. | A45D 26/0004 |
| 2020/0253811 A1* | 8/2020 | Alexander ........... | A46B 13/008 |

OTHER PUBLICATIONS

"Specimen." Merriam-Webster.com Dictionary, Merriam-Webster, https://www.merriam-webster.com/dictionary/specimen. Accessed Feb. 18, 2021. (Year: 2021).*
Wikipedia, Accelerometer, 2021. (Year: 2021).*
Recharge, The Batteries Report 2018, Apr. 18, 2018. (Year: 2018).*
He, Facial Cleansing Instrument (Year: 2019).*

* cited by examiner

PORTABLE MULTI-FUNCTIONAL NON-INVASIVE BLACKHEAD REMOVER APPARATUS

INCORPORATION BY REFERENCE

This continuation in part application claims the benefit of priority to the filing date of U.S. non provisional design patent application No. 29/673,389, entitled "Blackhead Removing Unit", which was filed on Dec. 14, 2018, and which is incorporated herein by reference in its entirety.

FIELD OF INVENTION

This invention relates to the field of beauty care devices, in particular to a portable multifunctional non-invasive blackhead remover.

BACKGROUND OF THE INVENTION

It is no secret that humans, for millennia now, have put a high value on personal appearance and the pursuit of beauty. The global beauty market as of 2017 was valued at $445 billion U.S. dollars with market projections indicating an upward trend as the commercial market reaches a wider audience.

A significant portion of this market is directed to maintaining a healthy attractive complexion, with youthful and blemish free skin. There is a wide range of skin treatments offered in the market, everything from simple remedies to be applied to the skin, such as topical creams and and often invasive procedures that involve chemical peeling or laser resurfacing.

Despite this seemingly eternal pursuit for idealized skin, and the amount of money at play, there is still not a consensus on what is best to achieve this goal. Further, because both poor and rich are interested in clear skin, the expensive treatments that the affluent use are not economically viable for all. Even further, because an individual's personal appearance is very much internalized and personal, many people may not feel comfortable with one of the more intense or invasive treatments and prefer other options that they can undertake in their own home, at their own pace. Thus, there is a significant portion of the beauty market that would be interested in an easy to use, economical, versatile, skin-treatment device that they can use in the comfort and privacy of their own home.

Naturally, a personal portable beauty device that is used on a face must not be too big nor too invasive. Along the same line, the device should run on a battery. Furthermore, it is desirable that such a device can incorporate multiple beauty care functions while still being light weight, compact, less power consumption, etc.

Acne flare-ups are typically caused by the skin's pores becoming clogged with dirt, dead skin, or bacteria. The clogged pores may simply show the accumulation of debris as what is traditionally identified as a blackhead, usually a small dot on the skin, in the area of the clogged pore, which may be somewhat raised compared to the surrounding skin. These clogged pores may remain simply inert and only interrupt the skins appearance, other times they may progress and turn red, swell up, and turn into a pimple.

As both are seen as undesirable, many people will treat their skin with exfoliating treatments, either using abrasives which seek to exfoliate the outer dermis and remove excess dead skin and debris before problems arise or applying topical creams with an astringent mechanism by which the skin is induced into constricting such to promote the expulsion of the same debris.

Traditionally, a person "pops a pimple" or removes a pimple by using two hard surfaces on two opposite sides of the offending pore to compress and create the necessary pressure to cause the pimple expelled. While this is convenient in the sense that no tools are required, and the left and right index fingers would do the job, it is extremely problematic and disapproved by professional dermatologists for a number of reasons. The top reason is that the human hands, fingers, and particularly fingernails typically are going to be dirtier with debris than the surface of the face and other areas of the body. Given pimples are caused by dirty debris and bacteria, treating it with a dirty tool becomes self-defeating and often leads to more blackheads, or worse, the introduction of scratches from the fingernails and associated bacteria that lead to infection. Some people may not use fingers but use instead tweezers or other simple tools to pop pimples. However, if they do not properly disinfect the tools, they are likely to encounter the same sanitary and infection issues.

Even if pimple popping people took the steps to disinfect their pimple-popping tools, the pain caused by the pressure on the site of offending pore is very discomforting. The pain could be unbearable where the pore is already infected and the skin is raised up and red. As discussed above, there are more complicated procedures that a person can undertake, but often these procedures may be limited to being administer by a beautician or clinician in a professional setting utilizing expensive equipment.

As such, it is desirable that a personal portable blackhead remover device is made available for consumers for them to easily and effectively self-treat their own affected skin, with multiple easy-to-use functions that are perfected to avoid scratching or introducing additional excess debris to the skin.

OBJECTIVE OF THE INVENTION

It is the object of this invention to create a compact, portable, multipurpose blackhead removal device.

It is the object of this invention to include a negative pressure, vacuum component to promote the expulsion of debris from impacted pores, such that the user's skin receives minimal contact, and is relieved from using mechanical pressure from tools or fingers which might cause damage or promote infection.

It is further the object of this invention to include a conductive metallic plate whereby cooling or heating temperatures may be transferred to the user's skin.

It is further the object of this invention to include a vibrating element which may be used simultaneously with the heating element to achieve a therapeutic skin massage treatment for the skin surface.

It is an object of this invention to provide a light weight and portable skin care device with three particular skin care functions (1) a blackhead removal function which by the application of a negative pressure vacuum on a particular area of skin promotes the expulsion and removal of the blackhead; (2) a heat and cool function that is controlled by a CPU and PCBand (3) a vibration component.

As manipulating the skin in any fashion may cause swelling and irritation, it is an object of this invention to, by the same tool the end user is already holding, provide for a convenient and effective way to address said swelling.

It is an object of this invention to provide a cordless device.

It is an object of the invention to provide a wireless charger.

It is an object of the invention to provide a cordless and hand-held skin care device that can be manipulated like a large pencil.

SUMMARY OF THE INVENTION

In one aspect of the invention, an apparatus for removing blackheads and providing skin care treatments comprising a funnel body wherein the funnel body comprises a compartment, a first opening and a second opening; wherein the first opening and the second opening are bended about 45 degrees from an axial axis; wherein the first opening further comprises a vacuum tip that is detachable and the second opening further comprises a massage metal plate; the apparatus further comprises a vacuum pump, a CPU, and a PCB that are all disposed within the compartment; wherein the vacuum tip further comprises a vacuum filter that is disposed in between the vacuum tip and the vacuum pump; wherein the vacuum pump is controlled by the CPU and the PCB; wherein the funnel body further comprises a smart switch disposed on the outside wall thereof; wherein the smart switch is wired to and controlled by the CPU and the PCB; wherein the apparatus further comprises a lithium battery that powers the PCB, the CPU, and the pump; wherein the funnel body further comprises vent pores; wherein the apparatus further comprises a status light made of LED that is wired to and controlled by the CPU and the PCB, and powered by the lithium battery. In one embodiment, the apparatus further comprises a vibrator component. In one embodiment, the apparatus further comprises a radiator and a thermoelectric semiconductor chip; wherein the thermoelectric semiconductor chip is wired to and controlled by the CPU and the PCB; wherein the thermoelectric semiconductor chip is wired to the radiator; wherein the thermoelectric semiconductor chip, when powered on, makes the radiator warm or cool; wherein the radiator is disposed underneath the massage metal plate. In one embodiment, the apparatus further comprises a gyroscope that detects which skin care tool is being used. In one another aspect of the invention for removing blackheads and providing skin care treatments comprises Providing a funnel body that comprises a compartment, a first opening and a second opening; Bending the first opening and the second opening about 45 degrees from the axial axis of the funnel body; Providing the first opening with a vacuum tip that is detachable; Providing the second opening with a massage metal plate; Providing a vacuum pump, a CPU, and a PCB that are all disposed within the compartment; Providing the vacuum tip which comprises a vacuum filter that is disposed in between the vacuum tip and the vacuum pump; Controlling the vacuum pump with the CPU and the PCB; Providing the funnel body which comprises a smart switch disposed on the outside wall thereof; Wiring the smart switch to and controlling it by the CPU and the PCB; Providing a lithium battery that powers the PCB, the CPU, and the pump; Providing the funnel body which comprises vent pores; Providing the apparatus which comprises a status light made of LED that is wired to and controlled by the CPU and the PCB, and powered by the lithium battery. In one embodiment, providing the apparatus which comprises a fan component. In one embodiment, providing the apparatus which comprises a vibrator component. In one embodiment, providing the apparatus which comprises a radiator and a thermoelectric semiconductor chip; wherein wiring the thermoelectric semiconductor chip to and controlling it by the CPU and the PCB; wherein wiring the thermoelectric semiconductor chip to the radiator; wherein placing the radiator underneath the massage metal plate. In one embodiment, providing the apparatus which comprises a gyroscope that detects which skin care tool is being used.

BRIEF DESCRIPTION OF THE DRAWINGS

These and other features and advantages of the invention will not be described with reference to the drawings of certain preferred embodiments, which are intended to illustrate and not to limit the invention, and in which:

FIG. 7 illustrates another embodiment of the invention that comprises a wireless charging mechanism that comprises a cradle that is plugged in.

DETAILED DESCRIPTION OF THE DRAWINGS

The invention will be described in the context of a preferred embodiment unless otherwise indicated.

Figure 1:
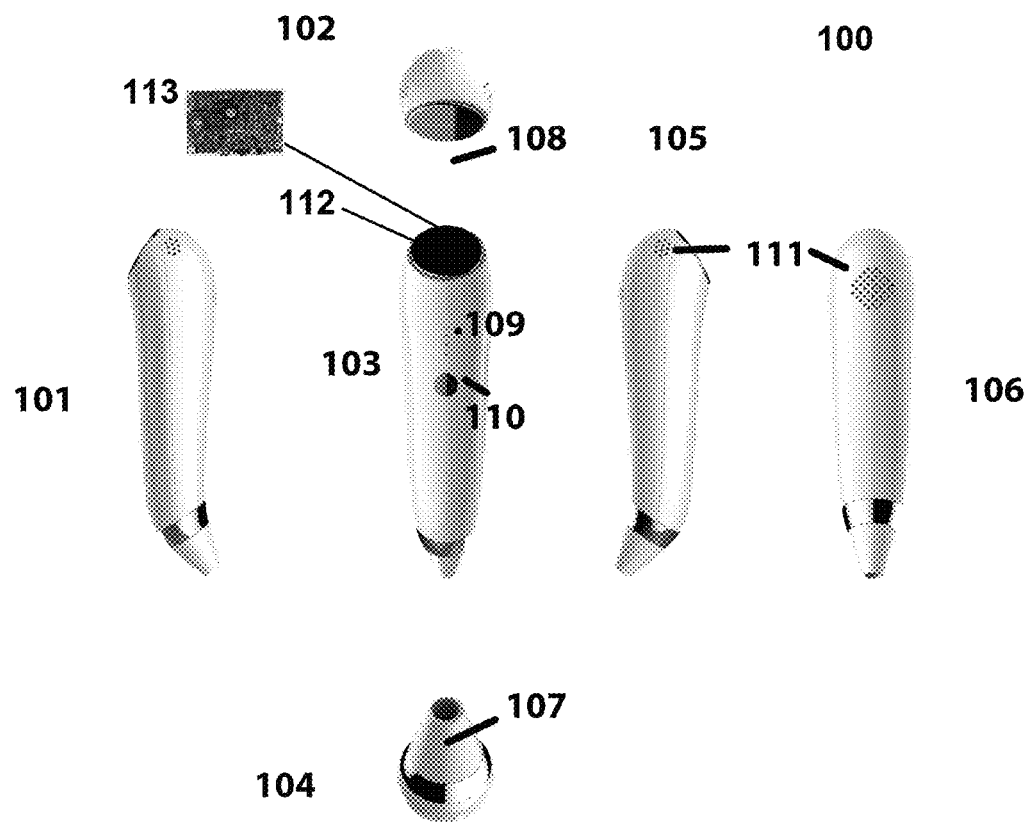
FIG. 1 illustrates an embodiment of this invention that comprises a vacuum suction tip at one end of the device, and heating/cooling/massaging plate located on the other end.

FIG. 1 illustrates the various orthographic views of an embodiment 100 of this invention, 101 illustrates the left side view, 103 front side view, 105 right side view, 106 back side view, 102 top side view, and 104 bottom side view. 101 shows an ergonomic form of the body of this embodiment. The body 101 is an elongated funnel tube with one end's opening diameter larger than the other's. The two ends are also bended about 45 degrees from the vertical axial axis to opposite directions. The bended ends allow comfortable holding of the device while using it.

The embodiment 100 further comprises a vacuum tip 107 And Operation button(s) 110 disposed on the front of the embodiment with a preference towards a minimalist approach, with this embodiment receiving all of its activation commands from a single button that may be pressed a different number of times, or perhaps held down vs pressed to activate different modes of the device. It is contemplated that the device itself by way of an internal gyroscope that might detect which orientation the device is held in, and activates either the vacuum 107 at the bottom 104 of the device or the massage plate 108 at the top 102 of the device.

The device further comprises status lights 109 which may communicate battery charge levels or other functions, and venting pores 111 to accommodate an internal vacuum component 112 disposed within the inner compartment in the body of the device. This embodiment further comprises a CPU and PCB 113 also disposed within the inner compartment of the body thereof. The CPU and PCB 113 controls the functions of the vacuum component. It, as well as the vacuum component, draws power from a lithium battery disposed within the compartment.

One end of the vacuum component 112 is attached to the vacuum tip 107. To prevent skin debris entering the vacuum's internal, the vacuum component comprises a replaceable suction filter disposed behind the vacuum tip 107. It is appreciated the suction filter can be made of a variety of materials, such as cotton, polyester mesh, etc. It is contemplated that the vacuum tip 107 be disposable and replaced at regular intervals like toothbrush heads. The vacuum component 112 further comprises an air suction pump that, when powered on and commanded by the CPU and PCB, creates suction at the vacuum tip 107. The air suction pump is attached to the other end of the vacuum component 112. The embodiment 100 further comprises a fan, a vibrator that is inset in a radiator, and a massage metal plate, all disposed at the end 102 of the embodiment 100. The fan, vibrator, and radiator are controlled by the CPU and PCB 113. The radiator is disposed under the massage metal plate. The radiator is connected to and controlled by a thermoelectric semiconductor chip, that is in turn connected to and controlled by the CPU and PCB main board. The thermoelectric chip makes the radiator warm or cool depending on the massage functions the user chooses. The radiator, in turn, makes the massage metal plate warm or cool. In addition to the warm and cool touches and massages, the inset vibrator can simultaneously vibrate and provides the simulation of a hand massage.

FIG. 1 further suggests various materials used in the construction of the embodiment 100. In an effort to keep production costs low, and thus the cost of the device to the consumer low, it is most likely that a majority of the surfaces are to be of molded injected plastic, or a lightweight, durable, non-corrosive metal. It is preferable that the device remain relatively lightweight as it is meant to be held comfortably in the hand of consumers of all ages, for various lengths of time. It is preferable that the material, whether plastic, metal, or composite, would be non-corrosive as it is likely that the device will be stored in a person's bathroom and be exposed to water and humidity.

This embodiment uses negative pressure to expel debris or blemish from a clogged pore. The user just places the vacuum tip 107 encircling the clogged pore and activates the suction function. The suction pump inside the body of this embodiment will create the negative pressure necessary to expel the blemish in the clogged pore. This method is beneficial for a number of reasons, (1) a small suction vacuum does not face the same limitations of creams and astringents, in that the device can be used many times without the additional purchase of a new amount of créme or chemical, further it is far easier for a person to spot treat a single area with such a device versus a cream that require time to either set in or cause the skin to have a discolored or greasy appearance; (2) a small suction vacuum is mechanically simple, and easily understood by the majority of consumer who would be familiar with a floor vacuum, as such, there is no special skill for an end user to learn to use the device as opposed to some of the more expensive and professional treatments; (3) the vacuum suction strength, when scaled to what is appropriate for one's skin, is low, so there is little to no risk that an end user might injure herself when the device is used as described; (4) while a vacuum does require a seal, such that the device will need to be placed to skin the same way tweezers or other tools, the seal can be created between the skin and the smoothed edges of the tip of the described vacuum tip such that the vacuum tip is not likely to cause scratching the way other tools might; and (5) the tip is easy and simple to be sanitized with a simple anti-bacterial fluid or process.

Immediately after clearing a clogged pore, the user can activate the cooling function of this embodiment and place the metal plate 108 near or on her pore to calm the skin swelling or irritation due to the prior blemish removal procedure.

Certainly, the warm or cool massage metal plate can be used independently of the blackhead remover function. The user can use the warm or cool massage functions for a preexisting irritation or stressed skin condition.

Figure 2:
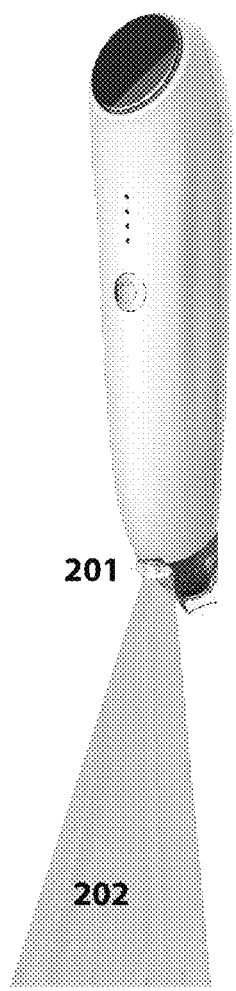
FIG. 2 illustrates an embodiment of this invention that comprises a LED light that allows a user to improve lighting on their targeted skin surface.

FIG. 2 illustrates another embodiment 200 of this invention that comprises a LED micro light element 201 mounted on the body of this embodiment. The user will be able to provide improved lighting 202 to their targeted skin surface when the light is on.

This is particularly useful as focused lighting is desirable when attempting such skin procedures. Further, because bathroom lighting is often fixed, or limited, the same principle extending to cosmetic mirrors, a light mounted on the vacuum end of the device will ensure a user an easier experience.

An LED micro light element is suggested and preferred in this embodiment as light diodes are inexpensive, dependable, have low battery draw, and can provide more than necessary lumen output for what is considered.

In this particular embodiment, the LED micro light 201 is activated by the same operation buttons 110 in FIG. 1, but as additional features are considered and contemplated, it may be necessary for the addition of additional device controls.

Figure 3:
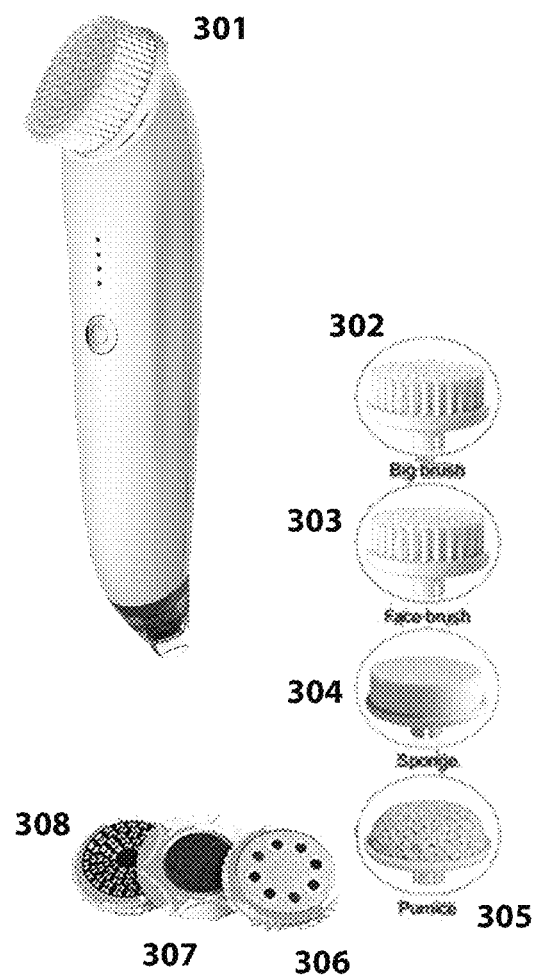
FIG. 3 illustrates an embodiment of this invention that comprises various therapeutic functions, such as scrubbing, or exfoliating surfaces, that might be mounted to a vibrating plate surface, either through mechanical means or temporary adhesives.

FIG. 3 illustrates an embodiment 300 of this invention that comprises various skin care tools. This embodiment comprises face brushes 301, 302, and face brush 303. It further comprises a sponge 304 and a pumice stone 305. It also comprises an abrasive pad 306, a scrubbing disc 307, and another abrasive disc 308. These various skin care tools are detachable and attachable to the massage metal plate. It is appreciated that there are several attachment mechanisms, such as magnets, clips, interlocking mechanical mechanism, or temporary adhesives. The vibrating of the metal plate causes an attached accessory brush or exfoliating pad to move and clean the skin.

Figure 4:
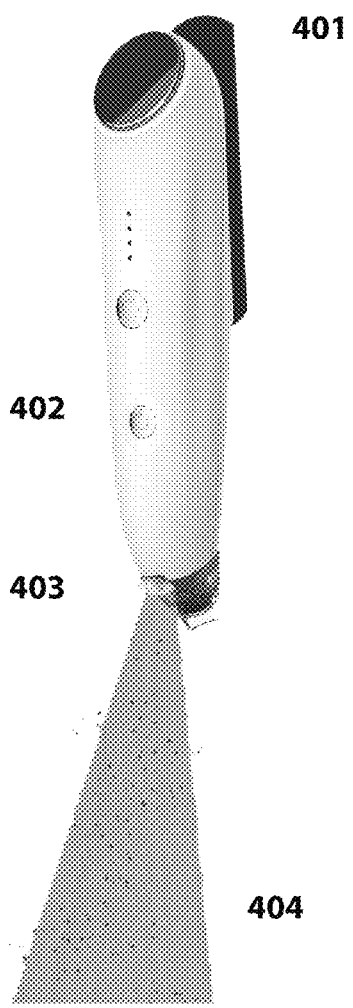
FIG. 4 illustrates another embodiment of this invention that comprises a spray mist function.

FIG. 4 illustrates another embodiment 400 of this invention that comprises a spray mist function. The embodiment 400 further comprises a pump to charge and expel the mist disposed within the compartment of the body of the device. Externally, we see the addition of a spray tip nozzle 403, an additional button 402 to control the sprayer, and the addition of a reservoir tank 401 which mounts and locks onto the device body. Many users, at the end of their skin care routine, uses the spray mist function to apply a toner to the skin. Toners refer to skin bracers or fresheners, skin tonics, or astringents.

All of these varieties of toner are typically used in a small quantity and are suspended in water such that they can be applied by way of a small amount of fine mist 404 which would be controlled by a simple button press 402. As such, it is possible to create a small volume reservoir 401 which would mount and accommodate such a function without significantly adding to the volume or weight of the overall device.

Figure 5:
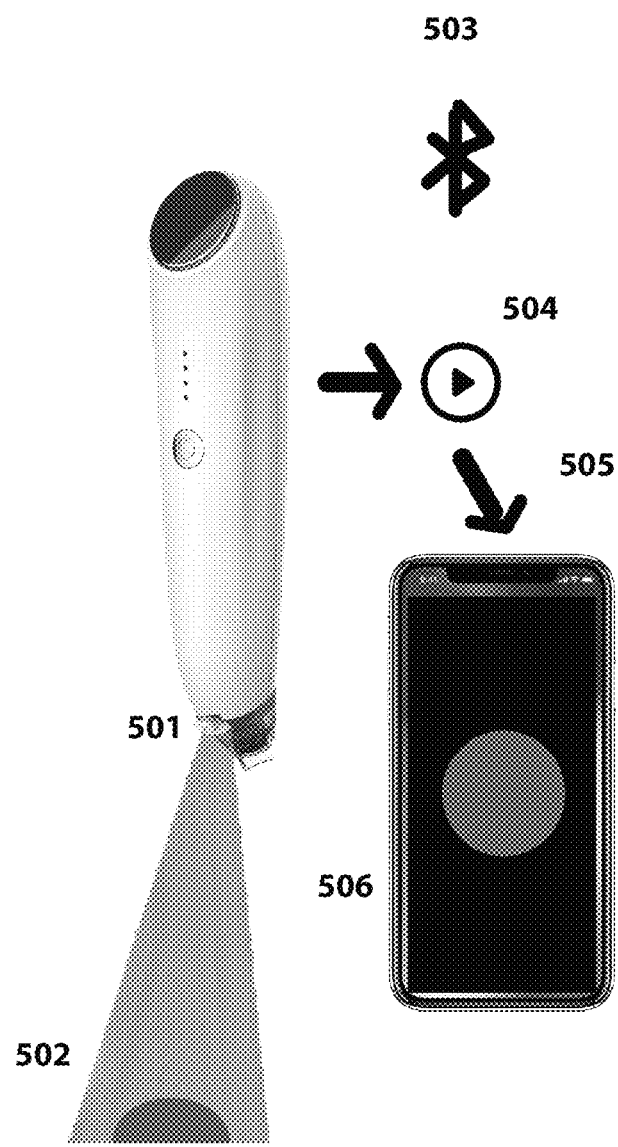
FIG. 5 illustrates another embodiment of this invention that comprises wireless components, such as Bluetooth, Wifi, NFC, etc.

FIG. 5 illustrates another embodiment 500 of this invention that comprises a wireless communication functionality, such as Bluetooth. This embodiment further comprises a camera 501 capable of sending video data feed via the wireless communication to a display device 505 via, such as a smartphone or tablet. The camera 501 is disposed on the body of the embodiment. The camera 501 allows a user to see skin areas 502 with more detail and magnification, or areas that may be blur with a bathroom or cosmetic mirror.

The camera 501 would wirelessly pair to a user's mobile device 505, such as a cell phone or tablet, and transmit to it via Bluetooth protocol 503 nearly instantaneous video 504 to be displayed on the device's screen 506. The camera 501 would be of benefit, as oftentimes a blemish may be in an area that is hard to maneuver and accurately target using sight by mirror or touch. By using this wireless camera function, a user would be able to quickly and accurately target the blemishes.

In another embodiment, the camera to device functionality is further developed with a software application that is more evolved than a video feed, and the software application comprises an component to take still images. For purpose of tracking a treatment's progress, before and after images may be captured and compared to see if skin complexion improves over the course of treatment.

Figure 6:
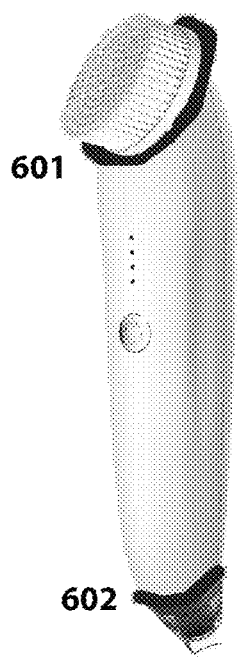
FIG. 6 illustrates another embodiment of the invention that comprises led light strip indicators and an internal pressure detection mechanism.

FIG. 6 illustrates another embodiment 600 of the invention that comprises LED light strip indicators 601 and 602, as well as an internal pressure detection mechanism whereby the LED light strips will light up or blink to indicate if a user is applying more pressure than is recommended. The lights and sensors work to indicate to the user if excessive pressure is being applied on her skin. The embodiment 600 further comprises a timer component that is connected to the LED light strips, which is the indicator for the set time intervals.

The pressure sensor functionality is particularly helpful for the massage or exfoliating functionality as disclosed above. A user can set a threshold pressure before a treatment session, and the pressure sensor functionality will alert the user if the current pressure crosses the threshold. Furthermore, the user can set the time duration for the session. The timer component will alert her when the timer goes off. It is further contemplated that the indicator is further developed by incorporating blinking, different colors of light, etc.

As is now commonly seen with many commercial wireless toothbrushes, professionals have declared a particular amount of application time sufficient to achieve results. With these tooth brushes, a light will flash, indicating that the user may now stop.

Now applying this same technology to the massage or exfoliating function, a user may wish for the device to apply an equal amount of time and thus effort on all areas of their skin. Watching a clock or stopwatch is inconvenient, and it is simple enough to incorporate an indicator into the device such that a person can use for, say 20 seconds on one side of their face, and then 20 seconds on the other symmetrical side.

Figure 7:

FIG. 7 illustrates an embodiment 700 of the invention that comprises a charging mechanism. In this embodiment, the wireless charging is achieved by way of a separate cradle 702 that is plugged in to a traditional electrical outlet. The separate cradle contains the necessary components such that it can wirelessly charge 703 the main units 701 lithium battery when the two components 701 and 702 are brought within close proximity of each other. Thus, the embodiment can be water-proof to protect the electronic component disposed within the compartment of the body of the device. Wireless capability and mobility allow the user the convenience of choosing when and where to use the device. Furthermore, wireless capability also allows a minimal and modern aesthetic look and feel.

By the main device 701 remaining wireless itself, a user is allowed maximum and uninterrupted mobility of the device, such that they do not need to concern themselves with a cord catching on other things on the countertop while their eyes are focused on making the necessary contact between the device and their skin surface.

It is nevertheless contemplated that in an alternative embodiment, there may be the addition of a USB-B or USB-C or other similar universal charging port such that a user, at the sacrifice of some aesthetic, might wired recharge the battery. This may be preferable in instances of extended travel where a device user foresees that they will require recharging but does not want to be burdened with the addition of the wireless base and wants to instead use an external cable or charging pack for many different devices.

The invention claimed is:

1. An apparatus for removing blackheads and providing skin care treatments comprising:
   a funnel body wherein said funnel body comprises a compartment, a first opening and a second opening;
      wherein said first opening and said second opening are bended about 45 degrees from an axial axis; and
      wherein said first opening further comprises a vacuum tip that is detachable and said second opening further comprises a massage metal plate;
   said apparatus further comprises a vacuum pump, a CPU, and a PCB that are all disposed within said compartment;
      wherein said vacuum tip further comprises a vacuum filter that is disposed in between said vacuum tip and said vacuum pump;
      wherein said vacuum pump is controlled by said CPU and said PCB;
      wherein said funnel body further comprises a smart switch disposed on the outside wall thereof; and
      wherein said smart switch is wired to and controlled by said CPU and said PCB;
   wherein said apparatus further comprises a lithium battery that powers said PCB, said CPU, and said pump;
      wherein said funnel body further comprises vent pores;
   wherein said apparatus further comprises a status light made of a LED that is wired to and controlled by said CPU and said PCB, and powered by said lithium battery;
   wherein said apparatus further comprises a gyroscope that detects which skin care tool is being used;
   wherein said apparatus further comprises a focus light made of a LED that illuminates a treated skin area and is wired to and controlled by said CPU and said PCB, and powered by said lithium battery;
   wherein said apparatus further comprises a radiator and a thermoelectric semiconductor chip;
      wherein said thermoelectric semiconductor chip is wired to and controlled by said CPU and said PCB;
      wherein said thermoelectric semiconductor chip is wired to said radiator;
      wherein said thermoelectric semiconductor chip, when powered on, makes said radiator warm or cool; and
      wherein said radiator is disposed underneath said massage metal plate.

2. A method for removing blackheads and providing skin care treatments comprises:
   providing a funnel body that comprises a compartment, a first opening and a second opening;
   bending said first opening and said second opening about 45 degrees from an axial axis of said funnel body;

providing said first opening with a vacuum tip that is detachable;

providing said second opening with a massage metal plate;

providing a vacuum pump, a CPU, and a PCB that are all disposed within said compartment;

providing said vacuum tip which comprises a vacuum filter that is disposed in between said vacuum tip and said vacuum pump;

controlling said vacuum pump with said CPU and said PCB;

providing said funnel body which comprises a smart switch disposed on an outside wall thereof;

wiring said smart switch to and controlling it by said CPU and said PCB;

providing a lithium battery that powers said PCB, said CPU, and said pump;

providing said funnel body which comprises vent pores;

providing a status light made of a LED that is wired to and controlled by said CPU and said PCB, and powered by said lithium battery;

providing a gyroscope that detects which skin care tool is being used;

providing a focus light made of a LED that illuminates a treated skin area and is wired to and controlled by said CPU and said PCB, and powered by said lithium battery;

wherein providing said apparatus which comprises a radiator and a thermoelectric semiconductor chip;

wherein wiring said thermoelectric semiconductor chip to and controlling it by said CPU and said PCB;

wherein wiring said thermoelectric semiconductor chip to said radiator; and wherein placing said radiator underneath said massage metal plate.

* * * * *